US012685716B1

(12) United States Patent (10) Patent No.: US 12,685,716 B1
Kennedy et al. (45) Date of Patent: *Jul. 21, 2026

(54) METHODS FOR INITIATING SOTALOL

(71) Applicants: Robert D. O. Kennedy, Traverse City, MI (US); Dina M. Kennedy, Traverse City, MI (US)

(72) Inventors: Robert D. O. Kennedy, Traverse City, MI (US); Dina M. Kennedy, Traverse City, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/940,629

(22) Filed: Nov. 7, 2024

Related U.S. Application Data

(63) Continuation of application No. 18/505,925, filed on Nov. 9, 2023.

(60) Provisional application No. 63/424,108, filed on Nov. 9, 2022.

(51) Int. Cl.
| | |
|---|---|
| *A61K 31/18* | (2006.01) |
| *A61B 5/318* | (2021.01) |
| *A61K 9/00* | (2006.01) |
| *A61N 1/39* | (2006.01) |
| *A61P 9/06* | (2006.01) |

(52) U.S. Cl.
CPC .............. *A61K 31/18* (2013.01); *A61B 5/318* (2021.01); *A61K 9/0019* (2013.01); *A61K 9/0053* (2013.01); *A61N 1/3962* (2013.01); *A61P 9/06* (2018.01)

(58) Field of Classification Search
CPC .... A61K 31/18; A61K 9/0019; A61K 9/0053; A61P 9/06; A61B 5/318; A61N 1/3962
See application file for complete search history.

(56) References Cited

U.S. PATENT DOCUMENTS

| | | | | |
|---|---|---|---|---|
| 2019/0380605 A1* | 12/2019 | Ivaturi | ................... | A61B 5/361 |
| 2020/0253903 A1* | 8/2020 | Somberg | ................ | A61K 31/18 |
| 2024/0148677 A1* | 5/2024 | Kennedy | ................ | A61K 31/18 |

OTHER PUBLICATIONS

M. Turakhia, et al. European Heart Journal, vol. 39, Issue 24, Jun. 21, 2018, pp. 2314-2325, https://doi.org/10.1093/eurheartj/ehy060 (Year: 2018).*
S. Dwivedi et al. Heart 2012; 98(Suppl 2): E1-E319, doi:10.1136/heartjnl-2012-302920v.3. (Only the Abstract). (Year: 2012).*

* cited by examiner

*Primary Examiner* — James H Alstrum-Acevedo
*Assistant Examiner* — Manahil Mirghani Ali Abdalhameed
(74) *Attorney, Agent, or Firm* — Holland & Hart LLP

(57) ABSTRACT

This disclosure describes a safe, effective, and novel method of preventing or treating atrial fibrillation, atrial flutter, atrial tachycardia, premature ventricular contractions, ventricular tachycardia, or a combination thereof using an initial intravenous sotalol dose followed by same day discharge and, in some cases, discharge following the administration of an intravenous dose of sotalol. This shortened time frame allows subjects to be discharged from the hospital less than 18 hours after sotalol initiation.

16 Claims, No Drawings

METHODS FOR INITIATING SOTALOL

CROSS-REFERENCE TO RELATED APPLICATIONS

This application is a continuation of U.S. patent application Ser. No. 18/505,925, filed Nov. 9, 2023, which claims the benefit of U.S. Provisional Patent Application No. 63/424,108, filed Nov. 9, 2022, each of which are incorporated by reference herein in their entirety.

BACKGROUND

Sotalol is a class III antiarrhythmic drug indicated for the maintenance of normal sinus rhythm (NSR) in those with atrial fibrillation (AF) and atrial flutter (AFL) resulting in a delay in time to recurrence.

Traditionally, initiation with oral sotalol requires a 3-day hospitalization due to the risks associated with the drug, including life-threatening ventricular arrhythmias such as Torsade de Pointes (Tdp) and polymorphic ventricular tachycardia associated with QTc prolongation. The degree of these adverse effects is directly proportional to the serum plasma concentration of sotalol. The maximum steady-state level is usually obtained after 5-6 oral doses with the most-commonly-prescribed twice-daily dosing. To reduce the risks of serious arrhythmias, the package insert requires all initiations to occur in a facility that can deliver continuous electrocardiographic monitoring and provide any interventions as a result of initiation.

In March 2020, the FDA approved a new method for the use of intravenous sotalol in AF subjects. The method includes a 1-day initiation of the drug, with the use of a single intravenous bolus dose followed by two additionally scheduled oral doses. The maximum QTc prolongation then presents sooner, allowing for faster stabilization of the drug with optimal oral sotalol dosing. This new protocol nevertheless requires an overnight hospital visit.

BRIEF SUMMARY

The present disclosure provides a method of safely and effectively initiating sotalol therapy for subjects over a significantly reduced period of time using an initial intravenous dose followed by same day discharge. The present disclosure also provides methods of safely and effectively converting AF/AFL to NSR and initiating long-term oral sotalol therapy for subjects utilizing intravenous sotalol. In particular, the method involves the administration of an intravenous dose of sotalol over 1 hour to a subject with AF/AFL followed by a single oral dose of sotalol after AF/AFL conversion and then discharge from the hospital and, in some cases, discharge following the administration of an intravenous dose of sotalol.

In some embodiments, the unique steps that differentiate this method from prior art include the reduced timeframe at which the subject is discharged home after the initial sotalol intravenous dose, thus further shortening the length of hospitalization relative to prior art protocols. All prior art would have subjects discharged from the hospital 18 hours or more after the initial sotalol intravenous dose, requiring subjects to receive a second dose of sotalol with a follow-up ECG prior to being discharged.

Nothing in this Summary section, the preceding Background, or the following Detailed Description shall limit any patent claim that matures from this disclosure. Any such patent claim shall instead be construed as would be understood by one of ordinary skill upon reviewing the plain text of the patent claim in the context of its claim dependency.

DETAILED DESCRIPTION

Definitions (1) The term "AF" stands for atrial fibrillation.

(2) The term "AFL" stands for atrial flutter.

(3) The term "AF/AFL" stands for atrial fibrillation and/or atrial flutter.

(4) The term "AT" stands for atrial tachycardia.

(5) The term "PVC" stands for premature ventricular contraction.

(6) The term "VT" stands for ventricular tachycardia.

(7) The term "NSR" stands for normal sinus rhythm.

(8) The term "RBBB" stands for right bundle branch block.

(9) The term "CrCl" stands for creatinine clearance.

(10) The term "IV" stands for intravenous.

(11) The term "PO" stands for "per os" and refers to an oral dosing regimen.

(12) The term "BID" stands for "bis in die" and refers to twice a day dosing.

(13) The term "QD" stands for "quaque die" and refers to once a day.

(14) The term "BP" stands for blood pressure.

(15) The term "HR" stands for heart rate.

(16) The term "renally impaired" refers to subjects having a creatinine clearance rate of <60 mL/min.

(17) The term "DCCV" stands for direct current cardioversion.

(18) The term "QT" refers to the interval measured from the start of the Q wave or the QRS complex, to the end of the T wave, where the Q wave corresponds to the beginning of ventricular depolarization and the T wave end corresponds to the end of ventricular repolarization.

(19) The term "QTc" refers to the calculated interval that represents the QT interval corrected for heart rate and can be derived by simple mathematical correlation of the QT interval and the heart rate.

(20) The term "ΔQTc" refers to the difference between a QTc measurement taken prior to the start of IV sotalol and a QTc measured after the start of IV sotalol (e.g., during loading or maintenance).

(21) Persistent cardiac arrhythmia refers to a condition selected from AF, AFL, AT, PVC, and VT.

(22) Sotalol refers to d,l-sotalol. Amounts of sotalol in milligrams (mg) refer to amounts of sotalol hydrochloride in mg (molecular weight 308.8) and not to amounts of molecular sotalol (molecular weight 272.4).

Sotalol is an antiarrhythmic agent indicated in subjects with AF/AFL who are currently in sinus rhythm and for the treatment of ventricular arrhythmias. Sotalol hydrochloride was previously approved by the FDA for intravenous administration and oral administration (e.g., 80 mg, 120 mg, and 160 mg tablets) to be administered twice daily. In the existing FDA-approved protocol, patients are hospitalized for >18 hours. Sotalol was not historically used in patients who are not in NSR.

Some aspects of this disclosure relate to the development of methods that allow subjects to be discharged from a medical facility that initiates IV sotalol less than 18 hours following initiation of IV sotalol, which avoids the requirement of an overnight hospital stay and provides other associated benefits. One of the innovations that allows earlier discharge is the use of IV sotalol as a converting medication in subjects that lack NSR, which is different from the current FDA-approved use of IV sotalol as a maintenance medication in patients that present with NSR.

In the current FDA-approved protocol, patients who lack NSR undergo DCCV to restore NSR prior to initiation of IV sotalol, which extends hospitalization. The inventors identified that IV sotalol can be utilized as a converting medication in patients who lack NSR, and thus, DCCV need not be performed prior to initiation of IV sotalol. DCCV may instead be performed following IV sotalol infusion, for example, in subjects who display AF following IV sotalol infusion to convert from AF to NSR. DCCV may be administered during an interval of time between IV sotalol infusion and a first oral dose of sotalol, for example, which does not extend hospitalization.

In some embodiments, sotalol injection is supplied in 10 mL single-dose vials, each containing 150 mg of sotalol hydrochloride as a clear solution (15 mg/mL).

The term "hospital" refers to medical facilities staffed and equipped to provide continuous electrocardiogram (ECG) monitoring and cardiac resuscitation to subjects, if needed. Typically, medical personnel at a hospital are trained in the management of serious life-threatening arrhythmias.

Reducing or shortening the length of a hospital stay refers to reducing/shortening the length of time a subject is admitted for oral sotalol initiation. For example, a subject would typically require a 3-day (72 hour) stay to be initiated on oral sotalol.

By administering sotalol according to the dosing protocol described herein, a subject can be discharged from a medical facility from 1 hour to less than 18 hours after initiation of intravenous sotalol administration. In some specific embodiments, a subject can be discharged from the medical facility from 5 hour to 11 hours after initiation of intravenous sotalol administration.

In some embodiments, the method comprises discharging the subject from the medical facility 1 to 9.5 hours after initiation of intravenous sotalol administration.

In some embodiments, the method comprises discharging the subject from the medical facility less than 18 hours after receiving the subject for IV sotalol administration at a medical facility. In some specific embodiments, the method comprises discharging the subject from the medical facility 6 to 12 hours after receiving the subject for IV sotalol administration at a medical facility. In some very specific embodiments, the subject has a creatinine clearance of at least 60 milliliters per minute, and the method comprises discharging the subject from the medical facility from 6 to 10 hours after receiving the subject for IV sotalol administration at a medical facility. In some very specific embodiments, the subject has a creatinine clearance of less than 60 milliliters per minute, and the method comprises discharging the subject from the medical facility from 9 to 12 hours after receiving the subject for IV sotalol administration at a medical facility.

In some embodiments, this disclosure provides a method of safely and effectively administering sotalol to a subject in need thereof, the method comprising intravenously administering sotalol over a period of one hour followed by a single dose of oral sotalol per protocol with the timing depending on the renal function of the subject prior to discharge less than 18 hours from initiation of intravenous administration of sotalol.

In some embodiments, the disclosure provides a method of reducing a hospital stay in a subject in need of treatment or prevention of AF, AFL, AT, PVCs, VT, or a combination thereof, the method comprising introducing a subject to sotalol administered intravenously over a period of 1 hour.

In some embodiments, the appropriate oral dose can be administered between about 4 hours and about 6 hours after completing intravenous administration.

In some embodiments, the subject is a human subject. In some specific embodiments, the subject is a human subject who presents with AF, AFL, AT, PVCs, VT, or a combination thereof.

Example Sotalol Protocol

1. After admission, obtain baseline parameters including QTc interval, HR, BP.
2. Infuse the IV sotalol loading dose over 1 hour.
3. Monitor QTc interval, HR, BP every 15 minutes during infusion.
4. Administer first oral dose at the appropriate time based on renal function. For CrCl≥60 mL/min, oral administration time is planned 4 hours following the completion of IV infusion. For CrCl=30-59 mL/min, oral administration time is planned 6 hours following the completion of IV infusion.
5. Obtain monitoring parameters including QTc interval, HR, BP at about 2 hours after oral administration.
6. Discharge subject from a medical facility at provider's discretion with instructions on subsequent sotalol dosing and scheduled clinic visits for additional follow-up.

Table 1 illustrates an innovative protocol that allows same-day discharge of a subject following initiation of IV sotalol and a first oral dose of sotalol.

TABLE 1

| Administration of Sotalol and Same-Day Discharge | | | | |
| --- | --- | --- | --- | --- |
| | CrCl ≥ 60 mL/min | | CrCl 30-59 mL/min | |
| Novel Protocol | Time | Actual Timing | Time | Actual Timing |
| Initiation of IV sotalol with q15 min QTc monitoring (infused over 1 hour) | Hour 0 | 11:00 | Hour 0 | 07:00 |
| IV Sotalol completion | Hour 1 | 12:00 | Hour 1 | 08:00 |
| 1st PO sotalol administration (4-6 hours after IV completion) | Hour 5 | 16:00 | Hour 7 | 14:00 |
| ECG (2 hours after oral dose) | Hour 7 DISCHARGE | 18:00 | Hour 9 DISCHARGE | 16:00 |
| 2nd PO sotalol administration (at home) | Hour 17 | 06:00 (next day and pushed back 2 | Hour 31 | 14:00 |

TABLE 1-continued

| Administration of Sotalol and Same-Day Discharge | | | | |
| --- | --- | --- | --- | --- |
| | CrCl ≥ 60 mL/min | | CrCl 30-59 mL/min | |
| Novel Protocol | Time | Actual Timing | Time | Actual Timing |
| ECG (in clinic next day) | Hour 19 | hours for dosing convenience) 08:00 | Hour 33 | (next day) 16:00 |

Table 2 illustrates an innovative protocol that allows same-day discharge of a subject following initiation of IV sotalol, in which a first oral dose of sotalol is consumed following discharge.

TABLE 2

| Initiation of IV Sotalol and Subsequent Discharge | | | | |
| --- | --- | --- | --- | --- |
| | CrCl ≥ 60 mL/min | | CrCl 30-59 mL/min | |
| Novel Protocol | Time | Actual Timing | Time | Actual Timing |
| Initiation of IV sotalol with q15 min QTc monitoring (infused over 1 hour) | Hour 0 | 10:00 | Hour 0 | 07:00 |
| IV Sotalol completion | Hour 1 DISCHARGE | 11:00 | Hour 1 DISCHARGE | 08:00 |
| $1^{st}$ PO sotalol administration (at HOME 4-6 hours after IV completion) | Hour 5 | 15:00 | Hour 7 | 14:00 |
| ECG (2 hours after oral dose in clinic same day) | Hour 7 | 17:00 | Hour 9 | 16:00 |

Various aspects of this disclosure relate to a method of initiating sotalol, comprising receiving a subject for intravenous (IV) sotalol administration at a medical facility, administering an initial IV dose of sotalol to the subject, and discharging the subject from the medical facility less than 18 hours after the initial IV dose.

In some embodiments, the method comprises receiving the subject and discharging the subject on the same calendar day.

In some embodiments, the method comprises receiving the subject and discharging the subject within less than 18 hours. In some specific embodiments, the method comprises receiving the subject and discharging the subject within no greater than 12 hours. In some very specific embodiments, the method comprises receiving the subject and discharging the subject within 6 to 12 hours.

In some embodiments, the method comprises discharging the subject less than 18 hours after administering the initial IV dose of sotalol. In some specific embodiments, the method comprises discharging the subject no greater than 10 hours after administering the initial IV dose of sotalol. In some very specific embodiments, the method comprises discharging the subject no greater than 7 hours after administering the initial IV dose of sotalol.

In some embodiments, the method comprises discharging the subject no greater than 1 hour after administering the initial IV dose of sotalol.

In some embodiments, the method comprises administering a first oral dose of sotalol to the subject after administering the initial IV dose.

In some embodiments, the method comprises providing instructions to the subject for taking the first oral dose. In some specific embodiments, the method comprises providing instructions to the subject for taking the first oral dose, wherein the subject consumes the first oral dose after discharge from the medical facility. In some very specific embodiments, the method comprises providing instructions to the subject for taking the first oral dose, wherein the subject presents with normal sinus rhythm, and the subject consumes the first oral dose after discharge from the medical facility.

In some embodiments, the method comprises (1) administering a first oral dose of sotalol to the subject after administering the initial IV dose; and (2) performing a first subsequent ECG on the subject, wherein the subject consumes the first oral dose of sotalol prior to the first subsequent ECG. In some specific embodiments, the method comprises (1) administering a first oral dose of sotalol to the subject after administering the initial IV dose; (2) performing a first subsequent ECG on the subject, wherein the subject consumes the first oral dose of sotalol prior to the first subsequent ECG; (3) providing instructions to the subject for taking a second oral dose of sotalol, wherein the subject consumes the second oral dose after discharge from the medical facility; (4) receiving the subject for a second subsequent ECG at the same medical facility or at a different medical facility; and (5) performing the second subsequent ECG on the subject, wherein the subject consumes the second oral dose of sotalol prior to the second subsequent ECG, and the second subsequent ECG is performed as an outpatient test. In some very specific embodiments, the method comprises (1) receiving the subject for IV sotalol administration and discharging the subject on the same calendar day and (2) receiving the subject for the second subsequent ECG and performing the second subsequent ECG on a subsequent calendar day.

In some embodiments, the method comprises (1) providing instructions to the subject for taking a first oral dose of sotalol, wherein the subject consumes the first oral dose after discharge from the medical facility and (2) receiving the subject at the same medical facility or at the different medical facility for a first subsequent ECG following consumption of the first oral dose, wherein the first subsequent ECG is performed as an outpatient test.

The terms "first subsequent ECG" and "second subsequent ECG" do not exclude other ECGs that may be performed during the method. For example, a subject typically has an ECG performed at baseline and every fifteen minutes during the administering of the initial IV dose of sotalol. The term "subsequent" in "first subsequent ECG" and "second subsequent ECG" refer to ECGs that are performed subsequent to administering the initial IV dose of sotalol. The terms "first" and "second" in "first subsequent ECG" and "second subsequent ECG" are used to differentiate two different ECGs and do not require performance of any other ECG. A method in which a first subsequent ECG is performed, for example, does not require that a second subsequent ECG is also performed.

In some embodiments, the subject presents with PVCs.

In some embodiments, the subject presents with VT.

In some embodiments, the subject presents with NSR.

In some embodiments, the subject presents with persistent cardiac arrhythmia; and DCCV is performed on the subject. In some specific embodiments, the subject presents with persistent cardiac arrhythmia; and the method comprises performing DCCV on the subject. In some very specific embodiments, the subject presents with persistent cardiac arrhythmia; DCCV is performed on the subject; the DCCV converts the arrhythmia to NSR; and the DCCV is administered after the initial IV dose.

In some embodiments, persistent cardiac arrhythmia is AF, AFL, AT, PVC, or VT.

In some embodiments, the method comprises receiving lab results for the subject that identify a CrCl rate for the subject prior to receiving the subject at the medical facility, wherein the initial IV dose is determined based on the CrCl rate.

In some embodiments, the method comprises discharging the subject from the medical facility less than 18 hours after the initial IV dose. In some specific embodiments, the method comprises discharging the subject from the medical facility less than 10 hours after the initial IV dose. In some very specific embodiments, the method comprises discharging the subject from the medical facility less than 7 hours after the initial IV dose.

In some embodiments, the subject presents with a persistent cardiac arrhythmia, and the method comprises administering the initial IV dose of sotalol to the subject while the patient has the arrhythmia. Administering an initial IV dose of sotalol to a patient while the patient has arrhythmia is novel and counter-intuitive because sotalol was historically used to maintain NSR rather than to convert cardiac arrhythmia to NSR.

In some embodiments, administering the initial IV dose of sotalol to the subject is effective to convert the persistent cardiac arrhythmia into NSR.

In some embodiments, DCCV is not performed on the subject.

In some embodiments, the subject presents with a persistent cardiac arrhythmia; the method comprises administering the initial IV dose of sotalol to the subject while the patient has the arrhythmia; and the administering the initial IV dose of sotalol to the subject is effective to convert the arrhythmia into NSR. In some specific embodiments, the subject presents with a persistent cardiac arrhythmia; the method comprises administering the initial IV dose of sotalol to the subject while the patient has the arrhythmia; the administering of the initial IV dose of sotalol to the subject is effective to convert the arrhythmia into NSR; and DCCV is not performed on the subject.

In some embodiments, the subject presents with a persistent cardiac arrhythmia, the method comprises administering DCCV to the subject; the DCCV converts the arrhythmia to NSR; and the DCCV is administered after the initial IV dose and prior to discharging the subject from the medical facility. Administering DCCV on a subject who presents with persistent cardiac arrhythmia subsequent to an initial IV dose is novel and counter-intuitive because sotalol was historically used to maintain NSR rather than to convert cardiac arrhythmia to NSR.

In some embodiments, the method comprises administering a first oral dose of sotalol to the subject after administering the initial IV dose and administering DCCV to the subject after administering the first oral dose of sotalol to the subject.

In some embodiments, the subject presents with a persistent cardiac arrhythmia; the method comprises administering DCCV to the subject; the DCCV converts the arrhythmia to NSR; and the DCCV is administered prior to the initial IV dose.

Various aspects of this disclosure relate to a method of treating a subject having AF, AFL, or AT comprising performing a method described anywhere in this disclosure, wherein the subject presents with AF, AFL, or AT. In some specific embodiments, the method is effective to treat the AF, AFL, or AT. In some very specific embodiments, the method is effective to convert the AF, AFL, or AT to NSR.

Various aspects of this disclosure relate to a method of treating a subject having PVCs comprising performing a method described anywhere in this disclosure, wherein the subject presents with PVCs. In some specific embodiments, the method is effective to treat the PVCs.

Various aspects of this disclosure relate to a method of treating a subject having VT comprising performing a method described anywhere in this disclosure, wherein the subject presents with VT. In some specific embodiments, the method is effective to suppress the VT.

Exemplification

The following examples are descriptive and non-limiting of the methods described herein. Suitable modifications and adaptations of the variety of conditions, formulations, and other parameters normally encountered in the field, and which are obvious to those skilled in the art in view of this disclosure are within the spirit and scope of the invention.

Example 1. Initiation with IV Sotalol in a Subject with Persistent AF/AFL Followed by DCCV and Discharge at 7.5 Hours A male subject, age 83, with a history of hypertension, obesity, alcohol use, and persistent AF/AFL with baseline RBBB was admitted for initiation of sotalol therapy. At arrival, baseline labs were obtained, and the subject was placed on continuous electrocardiogra monitoring. An IV sotalol load of 82.5 mg was administered over a 1-hour infusion with QTc, HR, and BP measurements monitored every 15 minutes during the infusion. After completion, a direct current cardioversion (DCCV) was performed, and the subject subsequently converted from AF to NSR. The first oral dose of sotalol 80 mg was given 4 hours after the completion of the IV sotalol infusion. Two hours after oral administration, all monitoring parameters obtained were within normal limits and the subject remained in NSR. At the provider's discretion, the subject was discharged from the hospital 7.5 hours from the time of IV sotalol initiation with instructions on subsequent sotalol dosing and returning to the clinic the next morning for additional follow-up.

Example 2. Initiation with IV Sotalol in a Subject with Paroxysmal AF and PVCs, which Converted from AF to NSR, Followed by Discharge at 7 Hours A male subject, age 76, with a history of multi-vessel coronary artery disease, prior percutaneous coronary intervention, hypertension, ischemic cardiomyopathy, paroxysmal AF, and PVCs was admitted for initiation of sotalol therapy. At arrival, baseline labs were obtained, and the subject was placed on continuous electrocardiography monitoring. An IV sotalol load of 82.5 mg was administered over a 1-hour infusion with QTc, HR, and BP measurements monitored every 15 minutes during the infusion. After completion, the subject subsequently converted from AF to NSR. The first oral dose of sotalol 80 mg was given 4 hours after the completion of the IV sotalol infusion. Two hours after oral administration, all monitoring parameters obtained were within normal limits, and the subject remained in NSR. At the provider's discretion, the subject was discharged from the hospital 7 hours from the time of IV sotalol initiation with instructions on subsequent sotalol dosing and returning to the clinic the next morning for additional follow-up.

Example 3. Initiation with IV Sotalol in a Subject with Persistent AF Followed by DCCV and Discharge at 9 Hours A female subject, age 84, with a history of hypertension, obesity, and persistent AF was admitted for initiation of sotalol therapy. At arrival, baseline labs were obtained, and the subject was placed on continuous electrocardiography monitoring. An IV sotalol load of 75 mg was administered over a 1-hour infusion with QTc, HR, and BP measurements monitored every 15 minutes during the infusion. After completion, DCCV was performed, and the subject subsequently converted from AF to NSR. Due to renal impairment (CrCl 30 mL/min), the first oral dose of sotalol 80 mg was given 5.5 hours after the completion of the IV sotalol infusion. Two hours after oral administration, all monitoring parameters obtained including a QTc measurement were within normal limits, and the subject remained in NSR. At the provider's discretion, the subject was discharged from the hospital 9 hours from the time of IV sotalol initiation with instructions on subsequent sotalol dosing and returning to the clinic the next day for additional follow-up.

Example 4. Initiation with IV Sotalol in a Subject with Persistent AF Followed by DCCV and Discharge at 9.5 Hours A female subject, age 80, with a history of hypertension, mild mitral regurgitation, mild aortic insufficiency, and persistent AF was admitted for initiation of sotalol therapy. At arrival, baseline labs were obtained, and the subject was placed on continuous electrocardiography monitoring. An IV sotalol load of 75 mg was administered over a 1-hour infusion with QTc, HR, and BP measurements monitored every 15 minutes during the infusion. After completion, a DCCV was performed, and the subject subsequently converted from AF to NSR. Due to renal impairment (CrCl 38 mL/min), the first oral dose of sotalol 80 mg was given 6.5 hours after the completion of the IV sotalol infusion. Two hours after oral administration, all monitoring parameters obtained including a QTc measurement were within normal limits, and the subject remained in NSR. At the provider's discretion, the subject was discharged from the hospital 9.5 hours from the time of IV sotalol initiation with instructions on subsequent sotalol dosing and returning to the clinic the next day for additional follow-up.

Example 5. Initiation with IV Sotalol in a Subject with Persistent AF Followed by DCCV and Discharge at 9.5 Hours A female subject, age 83, with a history of pulmonary arterial hypertension, heart failure with preserved ejection fraction, right ventricular dysfunction, chronic obstructive pulmonary disease, obstructive sleep apnea, hypertension, and persistent AF was admitted for initiation of sotalol therapy. At arrival, baseline labs were obtained, and the subject was placed on continuous electrocardiography monitoring. An IV sotalol load of 75 mg was administered over a 1-hour infusion with QTc, HR, and BP measurements monitored every 15 minutes during the infusion. After completion, a DCCV was performed, and the subject subsequently converted from AF to NSR. Due to renal impairment (CrCl 37 mL/min), the first oral dose of sotalol 80 mg was given 5 hours after the completion of the IV sotalol infusion. Two hours after oral administration, all monitoring parameters obtained including a QTc measurement were within normal limits, and the subject remained in NSR. At the provider's discretion, the subject was discharged from the hospital 9.5 hours from the time of IV sotalol initiation with instructions on subsequent sotalol dosing and returning to the clinic the next day for additional follow-up.

Example 6. Initiation with IV Sotalol in a Subject with PVCs and Paroxysmal AF Followed by DCCV and Discharge at 9 Hours A female subject, age 76, with a history of hypertension, heart failure with preserved ejection fraction, noninsulin-dependent diabetes, obstructive sleep apnea, obesity, PVCs, and paroxysmal AF was admitted for initiation of sotalol therapy. At arrival, baseline labs were obtained, and the subject was placed on continuous electrocardiography monitoring. An IV sotalol load of 75 mg was administered over a 1-hour infusion with QTc, HR, and BP measurements monitored every 15 minutes during the infusion. After completion, a DCCV was performed, converting the subject from AF to NSR. Due to renal impairment (CrCl 41 mL/min), the first oral dose of sotalol 80 mg was given 5.5 hours after the completion of the IV sotalol infusion. Two hours after oral administration, all monitoring parameters obtained including a QTc measurement were within normal limits, and the subject remained in NSR. At the provider's discretion, the subject was discharged from the hospital 9 hours from the time of IV sotalol initiation with instructions on subsequent sotalol dosing and returning to the clinic the next day for additional follow-up.

Example 7. Initiation with IV Sotalol in a Subject with Persistent AF Followed by DCCV and Discharge at 8.5 Hours A male subject, age 66, with a history of hypertension, alcohol abuse, obstructive sleep apnea, and persistent AF was admitted for initiation of sotalol therapy. At arrival, baseline labs were obtained, and the subject was placed on continuous electrocardiography monitoring. An IV sotalol load of 60 mg was administered over a 1-hour infusion with QTc, HR, and BP measurements monitored every 15 minutes during the infusion. After completion, the subject failed to convert after the first DCCV attempt, remaining in AF. The first oral dose of sotalol 120 mg was given 5 hours after the completion of the IV sotalol infusion, and then a second DCCV was performed. The subject subsequently converted from AF to NSR. Two hours after oral administration, all monitoring parameters obtained were within normal limits and the subject remained in NSR. At the provider's discretion, the subject was discharged from the hospital 8.5 hours from the time of IV sotalol initiation with instructions on subsequent sotalol dosing and returning to the clinic the next morning for additional follow-up.

Example 8. Initiation with IV Sotalol in a Subject with Persistent AF Followed by DCCV and Discharge at 7 Hours A male subject, age 70, with a history of hypertension, chronic obstructive pulmonary disease, obstructive sleep apnea, and persistent AF was admitted for initiation of sotalol therapy. At arrival, baseline labs were obtained, and the subject was placed on continuous electrocardiography monitoring. An IV sotalol load of 82.5 mg was administered over a 1-hour infusion with QTc, HR, and BP measurements monitored every 15 minutes during the infusion. After completion, a DCCV was performed, and the subject subsequently converted from AF to NSR. The first oral dose of sotalol 80 mg was given 4 hours after the completion of the IV sotalol infusion. Two hours after oral administration, all monitoring parameters obtained were within normal limits and the subject remained in NSR. At the provider's discretion, the subject was discharged from the hospital 7 hours from the time of IV sotalol initiation with instructions on subsequent sotalol dosing and returning to the clinic the next morning for additional follow-up.

Example 9. Initiation with IV Sotalol in a Subject with Persistent AF Followed by DCCV and Discharge at 6 Hours A male subject, age 70, with a history of mitral valve repair, myocardial infarction, obesity, chronic obstructive pulmonary disease, non-insulin dependent diabetes, congestive heart failure, and persistent AF was admitted for initiation of sotalol therapy. At arrival, baseline labs were obtained, and the subject was placed on continuous electrocardiography monitoring. An IV sotalol load of 90 mg was administered over a 1-hour infusion with QTc, HR, and BP measurements monitored every 15 minutes during the infusion. After completion, a DCCV was performed, converting the subject from AF to NSR. The first oral dose of sotalol 120 mg was given 3.5 hours after the completion of the IV sotalol infusion. Two hours after oral administration, all monitoring parameters obtained were within normal limits and the subject remained in NSR. At the provider's discretion, the subject was discharged from the hospital 6 hours from the time of IV sotalol initiation with instructions on subsequent sotalol dosing and returning to the clinic the next morning for additional follow-up.

Example 10. Initiation with IV Sotalol in a Subject with Persistent AF Followed by DCCV and Discharge at 9 Hours A male subject, age 81, with a history of a coronary artery bypass surgery with aortic valve replacement, heart failure with preserved ejection fraction, mild-to-moderate mitral regurgitation, hypertension, and persistent AF was admitted for initiation of sotalol therapy. At arrival, baseline labs were obtained, and the subject was placed on continuous electrocardiography monitoring. An IV sotalol load of 75 mg was administered over a 1-hour infusion with QTc, HR, and BP measurements monitored every 15 minutes during the infusion. After completion, a DCCV was performed, and the subject subsequently converted from AF to NSR. Due to renal impairment (CrCl 56 mL/min), the first oral dose of sotalol 80 mg was given 6 hours after the completion of the IV sotalol infusion. Two hours after oral administration, all monitoring parameters obtained were within normal limits and the subject remained in NSR. At the provider's discretion, the subject was discharged from the hospital 9 hours from the time of IV sotalol initiation with instructions on subsequent sotalol dosing and returning to the clinic the next day for additional follow-up.

Example 11. Initiation with IV Sotalol in a Subject with Persistent AF Followed by DCCV and Discharge at 9 Hours A female subject, age 76, with a history of a coronary artery bypass surgery, hypertension, and persistent AF was admitted for initiation of sotalol therapy. At arrival, baseline labs were obtained, and the subject was placed on continuous electrocardiography monitoring. An IV sotalol load of 75 mg was administered over a 1-hour infusion with QTc, HR, and BP measurements monitored every 15 minutes during the infusion. After completion, a DCCV was performed, and the subject subsequently converted from AF to NSR. Due to renal impairment (CrCl 50 mL/min), the first oral dose of sotalol 80 mg was given 6 hours after the completion of the IV sotalol infusion. Two hours after oral administration, all monitoring parameters obtained were within normal limits and the subject remained in NSR. At the provider's discretion, the subject was discharged from the hospital 9 hours from the time of IV sotalol initiation with instructions on subsequent sotalol dosing and returning to the clinic the next day for additional follow-up.

Example 12. Initiation with IV Sotalol in a Subject with PVCs and Persistent AF Followed by DCCV and Discharge at 9 Hours A male subject, age 78, with a history of hypertension, current smoker, alcohol use, PVCs, and persistent AF was admitted for initiation of sotalol therapy. At arrival, baseline labs were obtained, and the subject was placed on continuous electrocardiography monitoring. An IV sotalol load of 75 mg was administered over a 1-hour infusion with QTc, HR, and BP measurements monitored every 15 minutes during the infusion. After completion, a DCCV was performed, and the subject subsequently converted from AF to NSR. Due to renal impairment (CrCl 53 mL/min), the first oral dose of sotalol 80 mg was given 6 hours after the completion of the IV sotalol infusion. Two hours after oral administration, all monitoring parameters obtained were within normal limits and the subject remained in NSR. At the provider's discretion, the subject was discharged from the hospital 9 hours from the time of IV sotalol initiation with instructions on subsequent sotalol dosing and returning to the clinic the next day for additional follow-up.

Example 13. General Sotalol Initiation Protocol

The instructions on subsequent oral sotalol dosing set forth in examples 1-12 generally include self-administration in an amount of 40-160 mg of oral sotalol every 12-24 hours for a total of 1-2 additional oral doses of sotalol. When a patient lacks NSR following IV sotalol infusion, then DCCV is administered prior to the first oral dose.

Example 14. Initiation with IV Sotalol in a Subject with Persistent AF Followed by DCCV and Discharge at 5.5-18 Hours A female subject, age 65, presents with a history of hypertension, obesity, obstructive sleep apnea, and persistent AF. The decision is made to initiate long-term oral sotalol therapy with the goal of converting her AF to maintain NSR. This is done by obtaining baseline labs and placing the subject on continuous electrocardiography monitoring at arrival. An IV sotalol loading dose is determined (ranging from 60-125 mg) based on the subject's oral target dose (ranging from 40-160 mg) and her baseline renal function. The sotalol loading dose is then administered over a 1-hour infusion with QTc, HR, and BP measurements monitored and recorded every 15 minutes during the infusion. After completion, a DCCV is performed to subsequently convert the subject from AF to NSR. If the subject's renal function is greater than or equal to 60 mL/min, then the first oral dose of sotalol (ranging from 40-160 mg) can be given 3.5-6 hours after the completion of the IV sotalol infusion. If the subject's renal function is less than 60 mL/min, then the first oral dose of sotalol (ranging from 40-160 mg) can be given 5-6.5 hours after the completion of the IV sotalol infusion. All monitoring parameters (QTc, HR, and BP measurements) are obtained two hours after oral administration. If these parameters are within normal limits, then the subject can be discharged from the hospital 5.5-18 hours from the time of IV sotalol initiation at the provider's discretion with instructions on subsequent oral sotalol dosing. A return clinic visit is scheduled for the next day for additional follow-up.

Example 15. Initiation with IV Sotalol in a Subject with Persistent AF and Discharge at 5.5-18 Hours A male subject, age 74, presents with a history of hypertension, ischemic cardiomyopathy, and persistent AF. The decision is made to initiate long-term oral sotalol therapy with the goal of converting his AF and to maintain NSR. This is done by obtaining baseline labs and placing the subject on continuous electrocardiography monitoring at arrival. An IV sotalol loading dose is determined (ranging from 60-125 mg) based on the subject's oral target dose (ranging from 40-160 mg) and his baseline renal function. The sotalol loading dose is then administered over a 1-hour infusion with QTc, HR, and BP measurements monitored and recorded every 15 minutes during the infusion. After completion, the subject spontaneously converts from AF to NSR. If the subject's renal function is greater than or equal to 60 mL/min, then the first oral dose of sotalol (ranging from 40-160 mg) can be given 3.5-6 hours after the completion of the IV sotalol infusion. If the subject's renal function is less than 60 mL/min, then the first oral dose of sotalol (ranging from 40-160 mg) can be given 5-6.5 hours after the completion of the IV sotalol infusion. All monitoring parameters (QTc, HR, and BP measurements) are obtained two hours after oral administration. If these parameters are within normal limits, then the subject can be discharged from the hospital 5.5-18 hours from the time of IV sotalol initiation at the provider's discretion with instructions on subsequent oral sotalol dosing. A return clinic visit is scheduled for the next day for additional follow-up.

Example 16. Initiation with IV Sotalol in a Subject with Persistent AF Following Initial DCCV and Discharge at 5.5-18 Hours A male subject, age 72, presents with a history of hypertension, obesity, noninsulin-dependent diabetes, obstructive sleep apnea, mild aortic insufficiency, and persistent AF. The decision is made to initiate long-term oral sotalol therapy with the goal of converting his AF and to maintain NSR. This is done by obtaining baseline labs and placing the subject on continuous electrocardiography monitoring at arrival. An IV sotalol loading dose is determined (ranging from 60-125 mg) based on the subject's oral target dose (ranging from 40-160 mg) and his baseline renal function. A DCCV is performed to convert the subject from AF to NSR prior to sotalol administration. The sotalol loading dose is then administered over a 1-hour infusion with QTc, HR, and BP measurements monitored and recorded every 15 minutes during the infusion. If the subject's renal function is greater than or equal to 60 mL/min, then the first oral dose of sotalol (ranging from 40-160 mg) can be given 3.5-6 hours after the completion of the IV sotalol infusion. If the subject's renal function is less than 60 mL/min, then the first oral dose of sotalol (ranging from 40-160 mg) can be given 5-6.5 hours after the completion of the IV sotalol infusion. All monitoring parameters (QTc, HR, and BP measurements) are obtained two hours after oral administration. If these parameters are within normal limits, then the subject can be discharged from the hospital 5.5-18 hours from the time of IV sotalol initiation at the provider's discretion with instructions on subsequent oral sotalol dosing. A return clinic visit is scheduled for the next day for additional follow-up.

Example 17. Initiation with IV Sotalol in a Subject with Persistent AF/AFL Followed by First Oral Dose then DCCV and Discharge at 5.5-18 Hours A male subject, age 82, presents with a history of hypertension, alcohol abuse, obstructive sleep apnea, and persistent AF/AFL. The decision is made to initiate long-term oral sotalol therapy with the goal of converting his AF and to maintain NSR. This is done by obtaining baseline labs and placing the subject on continuous electrocardiography monitoring at arrival. An IV sotalol loading dose is determined (ranging from 60-125 mg) based on the subject's oral target dose (ranging from 40-160 mg) and his baseline renal function. The sotalol loading dose is then administered over a 1-hour infusion with QTc, HR, and BP measurements monitored and recorded every 15 minutes during the infusion. If the subject's renal function is greater than or equal to 60 mL/min, then the first oral dose of sotalol (ranging from 40-160 mg) can be given 3.5-6 hours after the completion of the IV sotalol infusion. If the subject's renal function is less than 60 mL/min, then the first oral dose of sotalol (ranging from 40-160 mg) can be given 5-6.5 hours after the completion of the IV sotalol infusion. All monitoring parameters (QTc, HR, and BP measurements) are obtained two hours after oral administration. The subject remains in AF/AFL and a DCCV is performed to convert the subject to NSR. If parameters are within normal limits, then the subject can be discharged from the hospital 5.5-18 hours from the time of IV sotalol initiation at the provider's discretion with instructions on subsequent oral sotalol dosing. A return clinic visit is scheduled for the next day for additional follow-up.

Example 18. Initiation with IV Sotalol in a Subject with Persistent AF Presenting in NSR Followed by Discharge at 5.5-18 Hours A female subject, age 80, presents with a history of hypertension, obesity, obstructive sleep apnea, alcohol abuse, and persistent AF. The decision is made to initiate long-term oral sotalol therapy with the goal of converting her AF and to maintain NSR. This is done by obtaining baseline labs and placing the subject on continuous electrocardiography monitoring at arrival. Subject is found to be in NSR on arrival. An IV sotalol loading dose is determined (ranging from 60-125 mg) based on the subject's oral target dose (ranging from 40-160 mg) and her baseline renal function. The sotalol loading dose is then administered over a 1-hour infusion with QTc, HR, and BP measurements monitored and recorded every 15 minutes during the infusion. If the subject's renal function is greater than or equal to 60 mL/min, then the first oral dose of sotalol (ranging from 40-160 mg) can be given 3.5-6 hours after the completion of the IV sotalol infusion. If the subject's renal function is less than 60 mL/min, then the first oral dose of sotalol (ranging from 40-160 mg) can be given 5-6.5 hours after the completion of the IV sotalol infusion. All monitoring parameters (QTc, HR, and BP measurements) are obtained two hours after oral administration. If these parameters are within normal limits, then the subject can be discharged from the hospital 5.5-18 hours from the time of IV sotalol initiation at the provider's discretion with instructions on subsequent oral sotalol dosing. A return clinic visit is scheduled for the next day for additional follow-up.

Example 19. Initiation with IV Sotalol in a Subject with PVCs Followed by Discharge at 1-4 Hours A female subject, age 57, current smoker, presents with a history of hypertension, obesity, obstructive sleep apnea, and symptomatic PVCs. The decision is made to initiate long-term oral sotalol therapy with the goal of reducing PVC burden. This is done by obtaining baseline labs and placing the subject on continuous electrocardiography monitoring at arrival. Subject is found to be in NSR on arrival. An IV sotalol loading dose is determined (ranging from 60-125 mg) based on the subject's oral target dose (ranging from 40-160 mg) and her baseline renal function. The sotalol loading dose is then administered over a 1-hour infusion with QTc, HR, and BP measurements monitored and recorded every 15 minutes during the infusion. If these parameters are within normal limits, then the subject can be discharged from the hospital after IV sotalol infusion is complete at the provider's discretion with instructions on subsequent oral sotalol dosing. Oral dosing can range from 40-160 mg and given 4-6 hours for the first oral dose and 12-24 hours for the second oral dose, depending on renal function respectively. Additional monitoring parameters (QTc, HR, and BP measurements) are scheduled for follow-up during the return clinic visit.

Example 20. Initiation with IV Sotalol in a Subject with Persistent AF Presenting in NSR Followed by Discharge at 1-4 Hours A male subject, age 53, presents with a history of hypertension, alcohol abuse, mild aortic insufficiency, and persistent AF. The decision is made to initiate long-term oral sotalol therapy. This is done by obtaining baseline labs and placing the subject on continuous electrocardiography monitoring at arrival. An IV sotalol loading dose is determined (ranging from 60-125 mg) based on the subject's oral target dose (ranging from 40-160 mg) and his baseline renal function. Subject is found to be in NSR on arrival. The sotalol loading dose is then administered over a 1-hour infusion with QTc, HR, and BP measurements monitored and recorded every 15 minutes during the infusion. If the monitoring parameters are within normal limits, then the subject can be discharged from the hospital after IV sotalol infusion is complete at the provider's discretion with instructions on subsequent oral sotalol dosing. Oral dosing can range from 40-160 mg and given 4-6 hours for the first oral dose and 12-24 hours for the second oral dose, depending on renal function respectively. Additional monitoring parameters (QTc, HR, and BP measurements) are scheduled for follow-up during the return clinic visit.

Example 21. Initiation with IV Sotalol in a Subject with Persistent AF Followed by DCCV and Discharge at 1-4 Hours A female subject, age 63, presents with a history of hypertension, alcohol abuse, obstructive sleep apnea, and persistent AF. The decision is made to initiate long-term oral sotalol therapy. This is done by obtaining baseline labs and placing the subject on continuous electrocardiography monitoring at arrival. An IV sotalol loading dose is determined (ranging from 60-125 mg) based on the subject's oral target dose (ranging from 40-160 mg) and her baseline renal function. The sotalol loading dose is then administered over a 1-hour infusion with QTc, HR, and BP measurements monitored and recorded every 15 minutes during the infusion. After completion, a DCCV is performed to subsequently convert the subject from AF to NSR. If the monitoring parameters are within normal limits, then the subject can be discharged from the hospital after DCCV is complete at the provider's discretion with instructions on subsequent oral sotalol dosing. Oral dosing can range from 40-160 mg and be given 4-6 hours for the first oral dose and 12-24 hours for the second oral dose, depending on renal function respectively. Additional monitoring parameters (QTc, HR, and BP measurements) are scheduled for follow-up during the return clinic visit.

Articles such as "the," "a," and "an" can connote the singular or plural. Also, the word "or" when used without a preceding "either" (or other similar language indicating that "or" is unequivocally meant to be exclusive—e.g., only one of x or y, etc.) shall be interpreted to be inclusive (e.g., "x or y" means one or both x or y).

As used in this disclosure, the term "or" is defined as a logical disjunction (i.e., and/or) and does not indicate an exclusive disjunction unless expressly indicated as such with the terms "either", "unless", "alternatively", and words of similar effect.

The term "and/or" shall also be interpreted to be inclusive (e.g., "x and/or y" means one or both x or y). In situations where "and/or" or "or" are used as a conjunction for a group of three or more items, the group should be interpreted to include one item alone, all the items together, or any combination or number of the items.

The terms have, having, include, and including should be interpreted to be synonymous with the terms comprise and comprising. The use of these terms should also be understood as disclosing and providing support for narrower alternative embodiments where these terms are replaced by "consisting" or "consisting essentially of."

Unless otherwise indicated, all numbers or expressions, such as those expressing dimensions, physical characteristics, and the like, used in the specification (other than the claims) are understood to be modified in all instances by the term "approximately." At the very least, and not as an attempt to limit the application of the doctrine of equivalents to the claims, each numerical parameter recited in the specification or claims which is modified by the term "approximately" should be construed in light of the number of recited significant digits and by applying ordinary rounding techniques.

All disclosed ranges are to be understood to encompass and provide support for claims that recite any and all subranges or any and all individual values subsumed by each range. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

All disclosed numerical values are to be understood as being variable from 0-100% in either direction and thus provide support for claims that recite such values or any and all ranges or subranges that can be formed by such values. For example, a stated numerical value of 8 should be understood to vary from 0 to 16 (100% in either direction) and provide support for claims that recite the range itself (e.g., 0 to 16), any subrange within the range (e.g., 2 to 12.5) or any individual value within that range (e.g., 15.2).

The terms recited in the claims should be given their ordinary and customary meaning as determined by reference to relevant entries in widely used general dictionaries and/or relevant technical dictionaries, commonly understood meanings by those in the art, etc., with the understanding that the broadest meaning imparted by any one or combination of these sources should be given to the claim terms (e.g., two or more relevant dictionary entries should be combined to provide the broadest meaning of the combination of entries, etc.) subject only to the following exceptions: (a) if a term is used in a manner that is more expansive than its ordinary and customary meaning, the term should be given its ordinary and customary meaning plus the additional expansive meaning, or (b) if a term has been explicitly defined to have a different meaning by reciting the term followed by the phrase "as used in this document shall mean" or similar language (e.g., "this term means," "this term is defined as," "for the purposes of this disclosure this term shall mean," etc.). References to specific examples, use of "i.e.," use of the word "invention," etc., are not meant to invoke exception (b) or otherwise restrict the scope of the recited claim terms. Other than situations where exception (b) applies, nothing contained in this document should be considered a disclaimer or disavowal of claim scope.

The subject matter recited in the claims is not coextensive with and should not be interpreted to be coextensive with any embodiment, feature, or combination of features described or illustrated in this document. This is true even if only a single embodiment of the feature or combination of features is illustrated and described in this document.

What is claimed is:

1. A method of sotalol administration for treatment of one or more cardiac arrhythmias, comprising:

determining a creatinine clearance of a subject prior to admission at a medical facility;

receiving the subject for admission at a medical facility based at least in part on the creatinine clearance of the subject;

determining a baseline QT or QTc interval and vital signs of the subject;

administering to the subject an initial intravenous (IV) loading dose of sotalol hydrochloride over a period of up to 1 hour, wherein the IV loading dose is selected from an amount ranging from 60 mg to 125 mg responsive to determining the creatinine clearance of the subject;

determining a second QT or QTc interval of the subject;

determining that the second QT or QTc interval is within a selected range, wherein the selected range is less than about 500 msec or less than about 550 msec for ventricular conduction delay;

administering oral sotalol hydrochloride to the subject responsive to determining the second QT or QTc interval is within the selected range including:

administering a first oral dose of 40 mg to 160 mg after completion of the initial IV loading dose; and administering one or more subsequent oral dose(s) of 40 mg to 160 mg at about 12 hour, 24 hour, or 48 hour interval(s) after the first oral dose; and discharging the subject from the medical facility less than 10 hours after administering the initial IV dose, on a same calendar day.

2. The method of claim 1, further comprising:

administering the first oral dose of sotalol to the subject after administering the initial IV dose;

performing a first subsequent electrocardiogram (ECG) on the subject after administering the first oral dose of sotalol to the subject after administering the initial IV dose, wherein the subject consumes the first oral dose of sotalol prior to the first subsequent ECG;

providing instructions to the subject for taking a second oral dose of sotalol, wherein the subject consumes the second oral dose after discharge from the medical facility;

receiving the subject for a second subsequent ECG at the same medical facility or at a different medical facility; and performing the second subsequent ECG on the subject, wherein the subject consumes the second oral dose of sotalol prior to the second subsequent ECG, and the second subsequent ECG is performed as an outpatient test.

3. The method of claim 2, further comprising:

receiving the subject for IV sotalol administration and discharging the subject on the same day; and receiving the subject for the second subsequent ECG and performing the second subsequent ECG on a subsequent day.

4. The method of claim 1, further comprising:

providing instructions to the subject for taking a first oral dose of sotalol, wherein the subject consumes the first oral dose after discharge from the medical facility; and receiving the subject at the same medical facility or at a different medical facility for an ECG following consumption of the first oral dose, wherein the ECG is performed as an outpatient test.

5. The method of claim 1, further comprising:

providing instructions to the subject for taking a first oral dose, wherein:

the subject presents with normal sinus rhythm; and the subject consumes the first oral dose after discharge from the medical facility.

6. The method of claim 1, wherein:

the subject presents with persistent cardiac arrhythmia; and direct current cardioversion (DCCV) is performed on the subject.

7. The method of claim 1, wherein:

the subject presents with a persistent cardiac arrhythmia; and the method comprises administering the initial IV dose of sotalol to the subject while the subject has the persistent cardiac arrhythmia.

8. The method of claim 7, wherein administering the initial IV dose of sotalol to the subject is effective to convert the persistent cardiac arrhythmia to a normal sinus rhythm.

9. The method of claim 7, wherein direct current cardioversion (DCCV) is not performed on the subject.

10. The method of claim 7, wherein:

the method comprises administering direct current cardioversion (DCCV) to the subject;

the DCCV converts the persistent cardiac arrhythmia to a normal sinus rhythm; and the DCCV is administered after the initial IV dose and prior to discharging the subject from the medical facility.

11. The method of claim 7, further comprising:

administering a first oral dose of sotalol to the subject after administering the initial IV dose; and administering direct current cardioversion (DCCV) after administering the first oral dose of sotalol to the subject.

12. The method of claim 1, further comprising:

administering a first oral dose of sotalol to the subject after administering the initial IV dose; and administering direct current cardioversion (DCCV) to the subject after administering the first oral dose of sotalol to the subject, wherein:

the subject presents with a persistent cardiac arrhythmia prior to administering the initial IV dose, and the DCCV converts the persistent cardiac arrhythmia to a normal sinus rhythm.

13. The method of claim 1, wherein:

the subject presents with a persistent cardiac arrhythmia; and the method comprises administering direct current cardioversion (DCCV) to the subject;

the DCCV converts the persistent cardiac arrhythmia to a normal sinus rhythm; and the DCCV is administered prior to the initial IV dose.

14. The method of claim 1, wherein the subject is in sinus rhythm, not currently in sinus rhythm, or has been or will be converted to sinus rhythm with sotalol and/or cardioversion, and wherein sotalol hydrochloride is administered for the treatment.

15. The method of claim 1, wherein the method of sotalol administration for the treatment of the one or more cardiac arrhythmias comprises a subject presenting with one or more following cardiovascular conditions:

atrial tachycardia, atrial flutter, atrial fibrillation, premature ventricular contractions, and ventricular tachycardia.

16. The method of claim 1, wherein discharging the subject from the medical facility less than 10 hours after administering the initial IV dose avoids an overnight hospital stay.

* * * * *